(12) United States Patent
Chang et al.

(10) Patent No.: US 11,684,511 B2
(45) Date of Patent: Jun. 27, 2023

(54) IRRIGATION AND ASPIRATION SLEEVE FOR PHACOEMULSIFICATION

(71) Applicant: Johnson & Johnson Surgical Vision, Inc., Irvine, CA (US)

(72) Inventors: Matthew Chang, Torrance, CA (US); Branden J Tarkeshian, Orange, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 125 days.

(21) Appl. No.: 13/836,339

(22) Filed: Mar. 15, 2013

(65) Prior Publication Data
US 2014/0276377 A1    Sep. 18, 2014

(51) Int. Cl.
*A61F 9/007* (2006.01)
*A61M 1/00* (2006.01)

(52) U.S. Cl.
CPC .......... *A61F 9/00736* (2013.01); *A61M 1/85* (2021.05)

(58) Field of Classification Search
CPC .. A61M 1/0039; A61M 1/0058; A61M 1/008; A61M 1/0084; A61M 2039/0009; A61M 1/77; A61M 1/92; A61F 9/0008; A61F 9/00781; A61F 9/00745
USPC ............ 604/22, 35, 36, 43, 173, 334
See application file for complete search history.

(56) References Cited

U.S. PATENT DOCUMENTS

| 4,526,571 A | 7/1985 | Wuchinich |
| 4,530,356 A * | 7/1985 | Helfgott .............. A61F 9/00763 606/171 |
| 4,573,979 A | 3/1986 | Blake |
| 4,904,238 A * | 2/1990 | Williams ................ A61M 1/85 604/43 |
| 4,983,160 A | 1/1991 | Steppe et al. |
| 5,084,009 A * | 1/1992 | Mackool ............. A61F 9/00745 604/22 |
| 5,139,504 A | 8/1992 | Zelman |
| 5,151,084 A * | 9/1992 | Khek ............. A61B 17/320068 604/19 |
| 5,154,694 A | 10/1992 | Kelman |
| 5,472,441 A * | 12/1995 | Edwards ................ A61N 5/045 128/898 |

(Continued)

FOREIGN PATENT DOCUMENTS

EP    0627904 B1    11/1997
EP    1632205 A1    3/2006

(Continued)

OTHER PUBLICATIONS

International Search Report and Written Opinion for Application No. PCT/US2014/018547, dated Jun. 13, 2014, 9 pages.

(Continued)

*Primary Examiner* — Bhisma Mehta
*Assistant Examiner* — William R Frehe
(74) *Attorney, Agent, or Firm* — Johnson & Johnson Surgical Vision, Inc.

(57) ABSTRACT

An apparatus and method for a sleeve for use with a phacoemulsification handpiece, the sleeve having a body portion suitable for engaging a handpiece is disclosed. The tip portion of the sleeve may comprise at least one aspiration port and at least one rounded portion which may be suitable for use for surgery of the eye, and, more particularly, for use around the edge of a capsular bag.

14 Claims, 6 Drawing Sheets

(56) References Cited

U.S. PATENT DOCUMENTS

| | | | |
|---|---|---|---|
| 5,562,612 A | 10/1996 | Fox | |
| 5,653,724 A | 8/1997 | Imonti | |
| 5,709,698 A * | 1/1998 | Adams | A61B 17/32002 604/22 |
| 5,741,226 A | 4/1998 | Strukel et al. | |
| 5,873,851 A | 2/1999 | Nilsson | |
| 5,921,999 A * | 7/1999 | Dileo | A61F 9/00745 606/166 |
| 5,957,928 A | 9/1999 | Kirwan, Jr. | |
| 5,989,212 A * | 11/1999 | Sussman | A61F 9/00736 606/107 |
| 5,993,409 A | 11/1999 | Maaskamp | |
| 6,013,046 A | 1/2000 | Maaskamp et al. | |
| 6,039,715 A | 3/2000 | Mackool | |
| 6,256,859 B1 | 7/2001 | Stoddard et al. | |
| 6,340,355 B1 | 1/2002 | Barrett | |
| 6,423,074 B1 | 7/2002 | Chen | |
| 6,454,763 B1 | 9/2002 | Motter et al. | |
| 6,654,999 B2 | 12/2003 | Stoddard et al. | |
| 7,329,261 B2 | 2/2008 | Perkins | |
| 7,588,553 B2 | 9/2009 | Dewey | |
| 7,601,135 B2 | 10/2009 | Akahoshi | |
| 7,857,794 B2 | 12/2010 | Dimalanta et al. | |
| 7,967,775 B2 * | 6/2011 | Hong | A61M 3/0283 604/27 |
| 8,721,581 B2 | 5/2014 | Zolli | |
| 2001/0015562 A1 | 8/2001 | Uematsu et al. | |
| 2005/0234473 A1 * | 10/2005 | Zacharias | A61F 9/00745 606/107 |
| 2007/0219482 A1 | 9/2007 | Perkins | |
| 2008/0139994 A1 * | 6/2008 | Mackool | A61F 9/00745 604/22 |
| 2009/0093750 A1 * | 4/2009 | Herman | A61F 9/00745 604/22 |
| 2010/0036331 A1 * | 2/2010 | Sen | A61M 25/0097 604/263 |
| 2011/0092888 A1 * | 4/2011 | Gerg | A61F 9/00736 604/22 |
| 2011/0201995 A1 * | 8/2011 | Nallakrishnan | A61F 9/00736 604/22 |
| 2011/0319810 A1 * | 12/2011 | Ghannoum | A61F 9/00736 29/428 |
| 2012/0116290 A1 * | 5/2012 | Dimalanta | A61F 9/00736 604/22 |
| 2012/0157944 A1 * | 6/2012 | Cucin | A61M 1/84 604/319 |
| 2012/0172786 A1 | 7/2012 | Mackool | |
| 2012/0323166 A1 * | 12/2012 | Fitzgerald | A61F 9/00736 604/22 |
| 2013/0231605 A1 | 9/2013 | Walter | |

FOREIGN PATENT DOCUMENTS

| | | |
|---|---|---|
| EP | 1693027 B1 | 7/2008 |
| EP | 1943990 B1 | 3/2010 |
| EP | 1835873 B1 | 2/2012 |

OTHER PUBLICATIONS

Cataract Product Catalog, Global Version, Alcon, 2008-2009, 66 pages.
Storz, Capsule Guard, Bausch and Lomb, 2012.
Storz, Silicone, Bausch and Lomb, 2009, 2 pages.
Bausch & Lomb Incorporated, Capsule Guard IA Brochure, 2012, http://www.storzeye.com/PDF/CapsuleGuard%20Brochure_web.pdf.

* cited by examiner

IRRIGATION AND ASPIRATION SLEEVE FOR PHACOEMULSIFICATION

FIELD OF THE INVENTION

The instant disclosure relates to the irrigation and aspiration of a surgical site and, more particularly, to a sleeve for use with an ultrasonic phacoemulsification tip for providing irrigation and aspiration during a phacoemulsification procedure.

BACKGROUND

Phacoemulsification of cataractic lenses is a medically recognized technique which generally includes making of a corneal incision and the insertion of a hand held surgical implement, i.e., a handpiece, which includes a needle that is ultrasonically driven in order to emulsify the lens. The handpiece may be equipped to not only emulsify a lens, but further to provide a vacuum for aspiration of the emulsified lens, and also to provide irrigation for the insertion of fluids.

More particularly, this irrigation may be provided in order to maintain normal pressure within the eye during surgery. For example, a balanced salt solution (BSS) may be provided as an irrigation fluid, and may typically be supplied from an elevated chamber or bottle/bag.

Importantly, this irrigation, and the aforementioned aspiration of fluid through the eye, must be carefully monitored in order to maintain normal pressure within the eye during surgical procedures. For example, an under pressure condition may cause distortion of the eye, which may interfere with surgical procedures or may cause damage to the eye. On the other hand, overpressure may cause damage to the eye.

Furthermore, during surgical procedures, use of the handpiece to emulsify a cataract, for example, limits the usefulness of the handpiece to perform other functions. For example, an ultrasonic tip used to break up a cataract is not suitable for use with the softer and less dense peripheral cortex material of the cataract. Thus, in the known art, once the hard portion of a cataract is emulsified and/or broken up the physician must use a separate handpiece for only irrigation and aspiration to safely remove this softer material without damaging the eye.

The use of the second handpiece increases the time and expense of surgery and forces the physician to recalibrate and/or prime the handpiece to effectuate the proper pressures associate with the irrigation and aspiration aspects of the second handpiece. Further disruption and complications may also be introduced as the newly introduced second handpiece is required to be sterilized.

Thus, a need exists to allow the use of a single handpiece during phacoemulsification surgery while mitigating the adverse effects that attend the prior art.

SUMMARY OF THE INVENTION

An apparatus and method for a sleeve for use with a phacoemulsification handpiece is disclosed, the sleeve having a body portion suitable for engaging a phacoemulsification handpiece, and a tip portion. The tip portion of the sleeve may comprise at least one aspiration port, and at least one rounded portion which may be suitable for use for surgery of the eye, and, more particularly, for use around the edge of a capsular bag. The sleeve may attach to a phacoemulsification handpiece by the inclusion of a threaded female orifice.

The sleeve may also comprise a grip component to allow for ease of control by a user when attaching or removing the sleeve from the phacoemulsification handpiece, and may also comprise a detent, a raised portion, an etched portion and/or rubberized plastic, for example. Additionally, the sleeve may be sized to accommodate a portion of a needle assembly of the phacoemulsification handpiece, and may further comprise a curved tip.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical surgical, and particularly ophthalmic surgical, devices, systems, and methods. Those of ordinary skill may recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

The present invention may allow a phacoemulsification handpiece to be transformed into an irrigation/aspiration handpiece without the need to switch handpieces or to recalibrate the handpiece and/or the phacoemulsification system. In addition to minimizing disruption during the surgical process, and eliminating the need to switch handpieces or recalibrate a handpiece and/or the phacoemulsification system, the present invention may reduce the total time of the surgical procedure and may reduce potential errors with the recalibration of the phacoemulsification surgery system, thereby additionally lowering end-user costs and potential complications. Similarly, the use of the same handpiece may eliminate the need to prime either of the irrigation and/or aspiration sources, further increasing the realized time savings and potentially averting any complications which may be encountered if, for example, the system can not be timely primed while surgery is in process.

For example, after phacoemulsification has been completed using, for example, an ultrasonic titanium needle, a portion of the phacoemulsification tip and/or sleeve may be removed and the sleeve of the present invention may be placed over the remaining aspect of the phacoemulsification tip and/or sleeve for the purpose of continuing with the surgical procedure. Such continuation of the surgical procedure may include, for example, progressing with the removal of the softer cortex. The removed portion of the handpiece may, for example, include the existing irrigation sleeve, thus leaving the titanium needle on the handpiece.

Figure 1A:
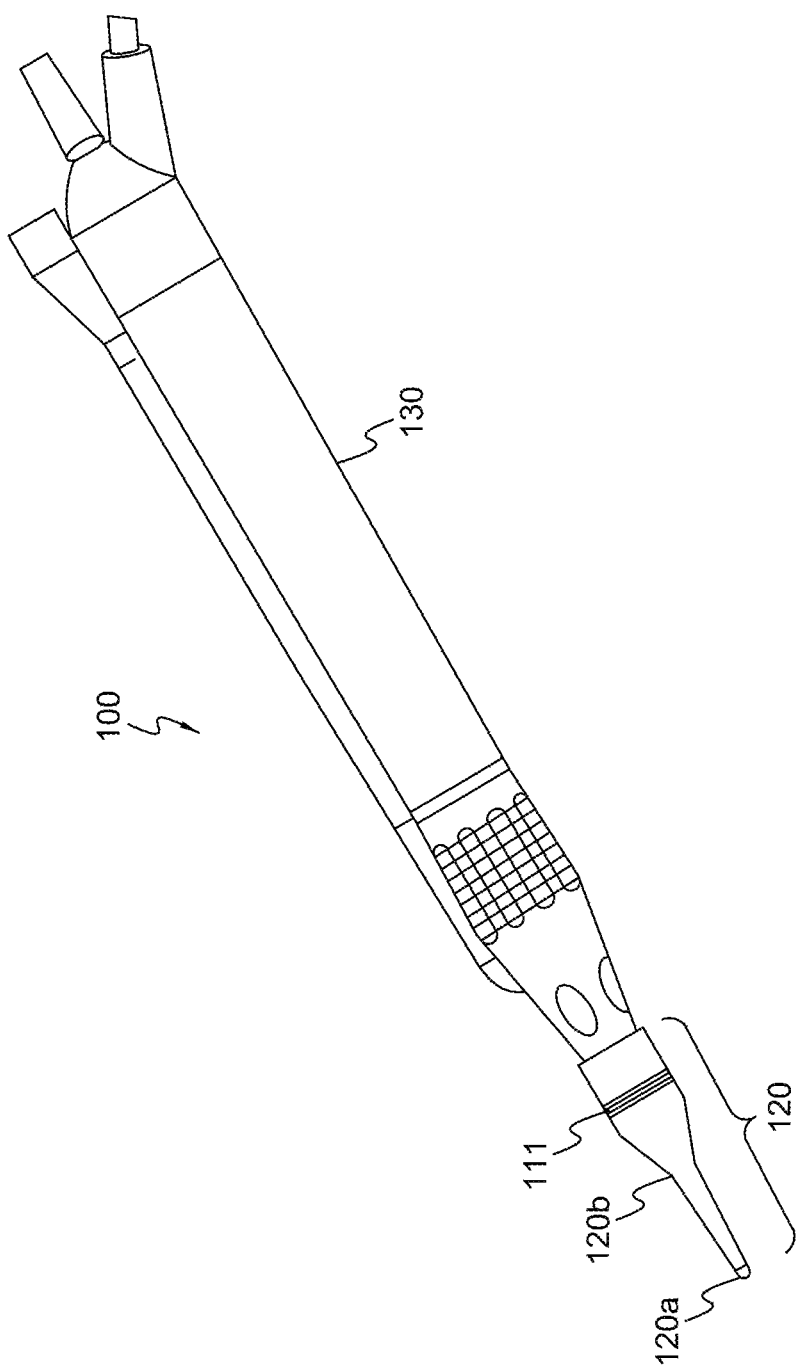
FIG. 1a illustrates a phacoemulsification handpiece suitable for use with the present invention.
Figure 1B:
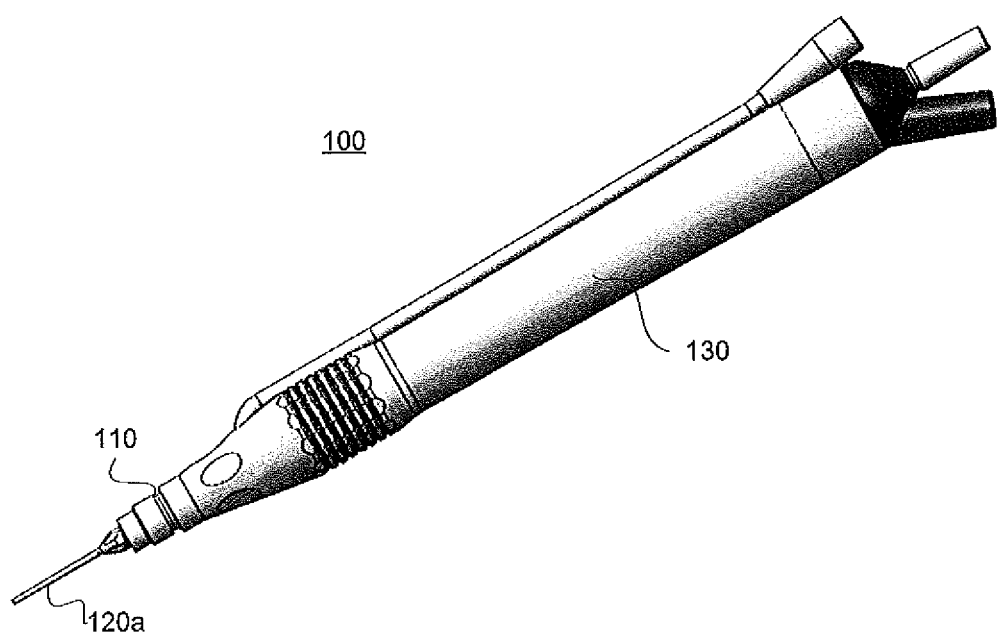
FIG. 1b illustrates a phacoemulsification handpiece suitable for use with the present invention.

As illustrated in FIGS. 1a and 1b, a phacoemulsification handpiece 100 may include a body 130 having a phaco needle assembly 120 at its distal end, and which is connected at its proximate end to a surgical system (not shown) which may provide the handpiece 100 with ultrasonic power, irrigation fluid, and an aspirating vacuum, for example. Additionally, the phaco needle assembly 120 may include a phaco needle 120a, a phaco sleeve 120b, or both. The phaco needle assembly 120 may provide an aspirating vacuum through the end of the needle portion of the phaco needle 120a assembly 120 and irrigation fluid to an eye via phaco sleeve 120b.

The handpiece 100 may also include at least one phaco sleeve attachment means 110, which may be located proximate to the distal end of handpiece 100 and may allow for the attachment of the phaco sleeve type peripheral, and at least one sleeve attachment means 111, which may be located proximate to the distal end of handpiece 100 or may be located on the exterior of the phaco sleeve 120b and may allow for the attachment of the sleeve. Attachment means 110 and 111, as described herein, includes any attachment mean associated with handpiece 100 and with phaco needle assembly 120 respectively. The phaco sleeve attachment means 110 and the sleeve attachment means 111 may include any known method of attaching a workpiece or other useful item to a phacoemulsification handpiece, and may further include, for example, a threaded portion, such as a threaded female orifice, an adhesive, at least one protrusion and receiving detent, and/or a locking mechanism, such as, for example, a groove and pin system.

Figure 2:
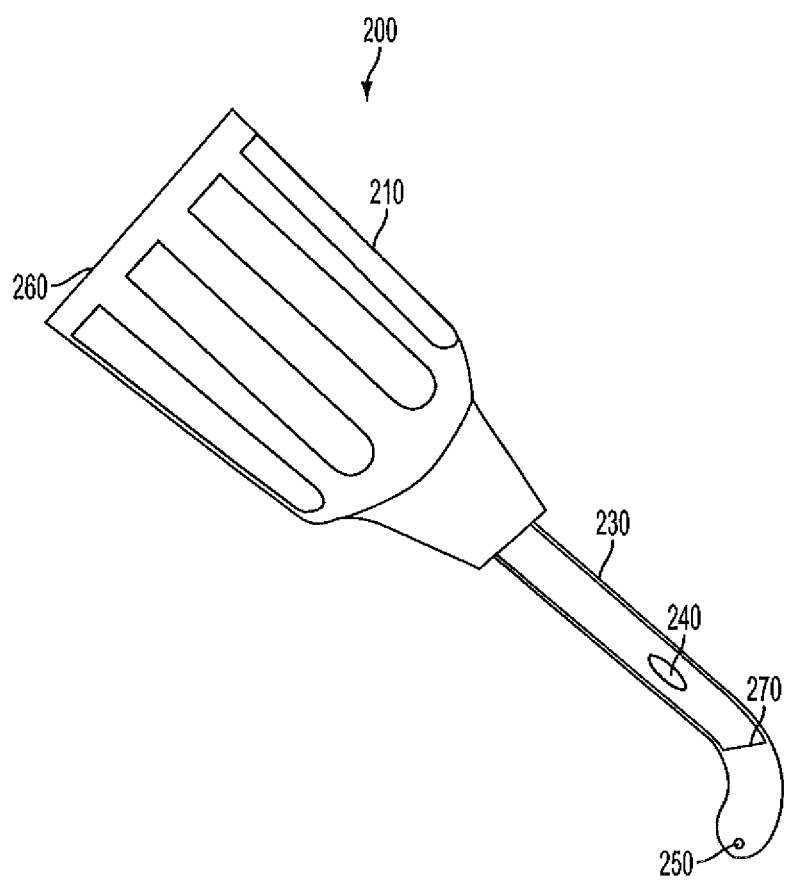
FIG. 2 illustrates an exemplary embodiment of a sleeve for use on a phacoemulsification handpiece.

FIG. 2 illustrates an embodiment of an irrigation and aspiration sleeve, which may be used with handpiece 100 and which may receive phaco needle tip 120a, or, in embodiments, phaco needle assembly 120 (which may include a phaco sleeve 120b). The sleeve may have a main body portion 210 and a tip 230. The distal end of body portion 210 may taper toward the tip 230, and the tip 230 may taper toward the distal end of sleeve 200. Further, the tip 230 may be constructed of surgical grade stainless steel, plastic, silicone, a combination of materials, and/or any other material known in the art to be suitable for use with phacoemulsification surgery and/or in a surgical environment. Preferably, the sleeve 200 is rigid with a rounded end suitable for use within the eye during surgery.

The body portion 210 may include an attachment means 260 which may be compatible with attachment means 111, and which may allow the proximate end of the body portion 210 to be proximate to body 130 of handpiece 100. The body portion 210 may comprise a portion suitable for providing an enhanced grip for handling and fastening the sleeve 200 to handpiece 100. Such a portion may include rubberized plastic (not shown), scoring/etching of the body portion 210 (shown), and/or at least one raised and/or detent areas (not shown).

The sleeve 200 may be sized to accommodate the phaco needle assembly 120 such that the distal end of the needle portion of the phaco needle assembly 120 may be positioned below the irrigation port 240 of tip 230. In this way, for example, the tip 230 may accommodate the entire needle portion of the phaco needle assembly 120, and irrigation port 240 may align with an irrigation port located on the phaco needle assembly 120 (not shown).

Thus, in an embodiment of the present invention, the phaco needle assembly 120 may be removed from handpiece 100, and sleeve 200 may be installed in its place, with attachment means 260 engaging the phaco sleeve attachment means 110 located on the handpiece 100. Alternatively, sleeve 200 may be installed over phaco needle assembly 120 and may engage the sleeve attachment means 111 located on the phaco needle assembly 120 with the attachment means 260.

As would be appreciated by those skilled in the art, the irrigation port 240 may be located on the sleeve in any position to match the existing phaco sleeve irrigation port of the phaco needle assembly 120. Similarly, attachment means 260, phaco sleeve attachment means 110, and sleeve attachment means 111 may be suitably configured to ensure alignment of the irrigation ports without undue care taken by the user. For example, the attachment means may provide for alignment of the irrigation ports when the attachment means are fully engaged and/or the user follows a visual identifier, such as, for example, the alignment of marking(s) on the sleeve 200 and the handpiece 100. Similarly, the irrigation port in the phaco needle assembly 120, for example, may be used for visual alignment with irrigation port 240, in embodiments wherein such alignment is needed or desired.

Figure 4A:
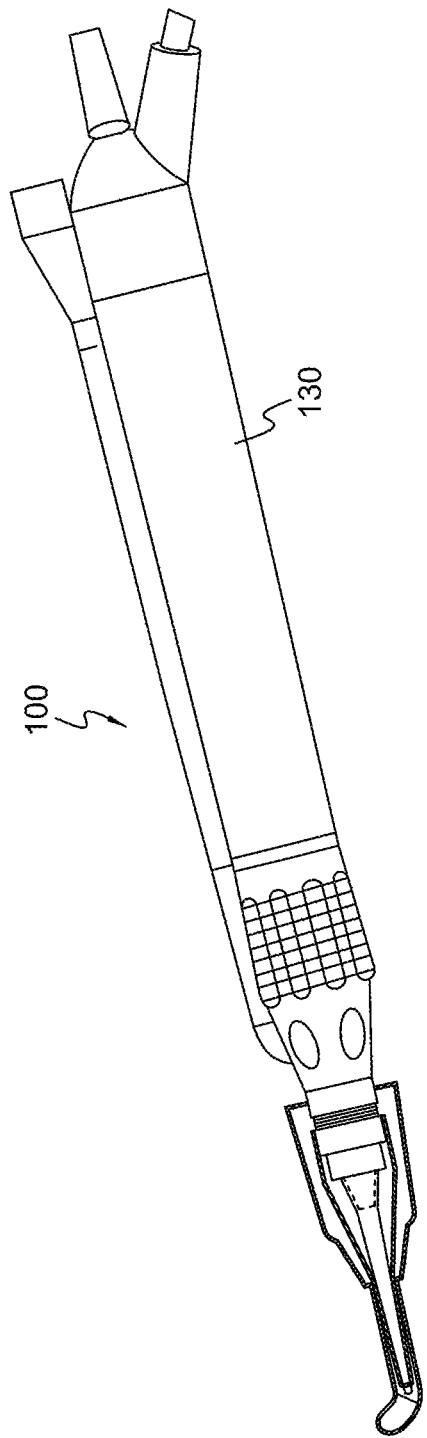
FIG. 4a illustrates an exemplary embodiment of a sleeve on a phacoemulsification handpiece.
Figure 4B:
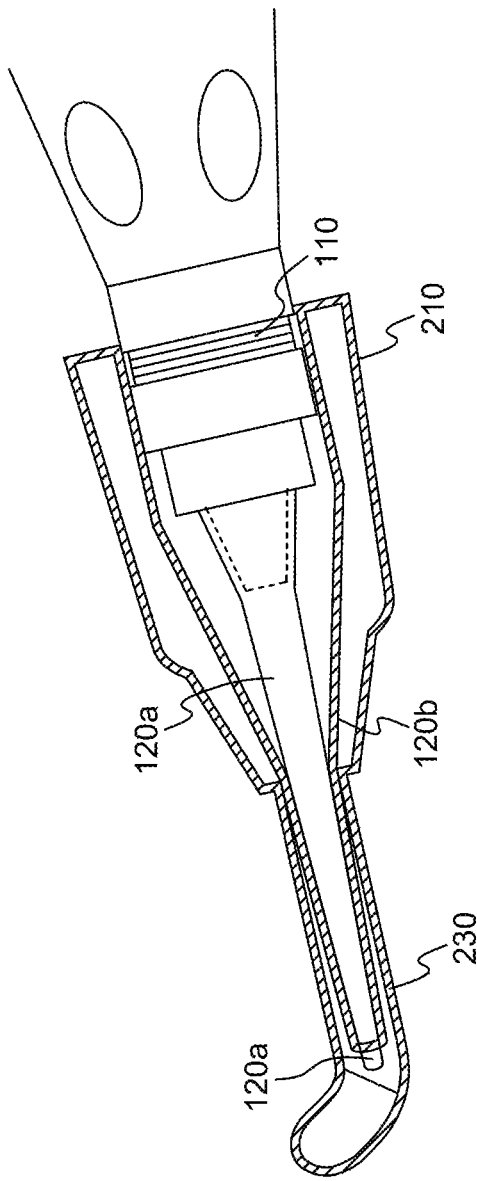
FIG. 4b illustrates a cross-section of an exemplary embodiment of a sleeve on a phacoemulsification needle assembly.

FIGS. 4a and 4b illustrate the body 130 of the phacoemulsification handpiece 100 having a phaco needle assembly 120 at its distal end. The phaco needle assembly 120 includes the phaco needle 120a and the phaco sleeve 120b. The phaco sleeve 120b substantially covers the phaco needle 120a. The phaco sleeve 120b is attached to the phaco sleeve attachment means 110. The body portion 210 is installed over the phaco needle 120a and the phaco sleeve 120b. The tip 230 of the body portion 210 accommodates the entire needle portion of the phaco needle 120a and phaco sleeve 120b.

Figure 5:
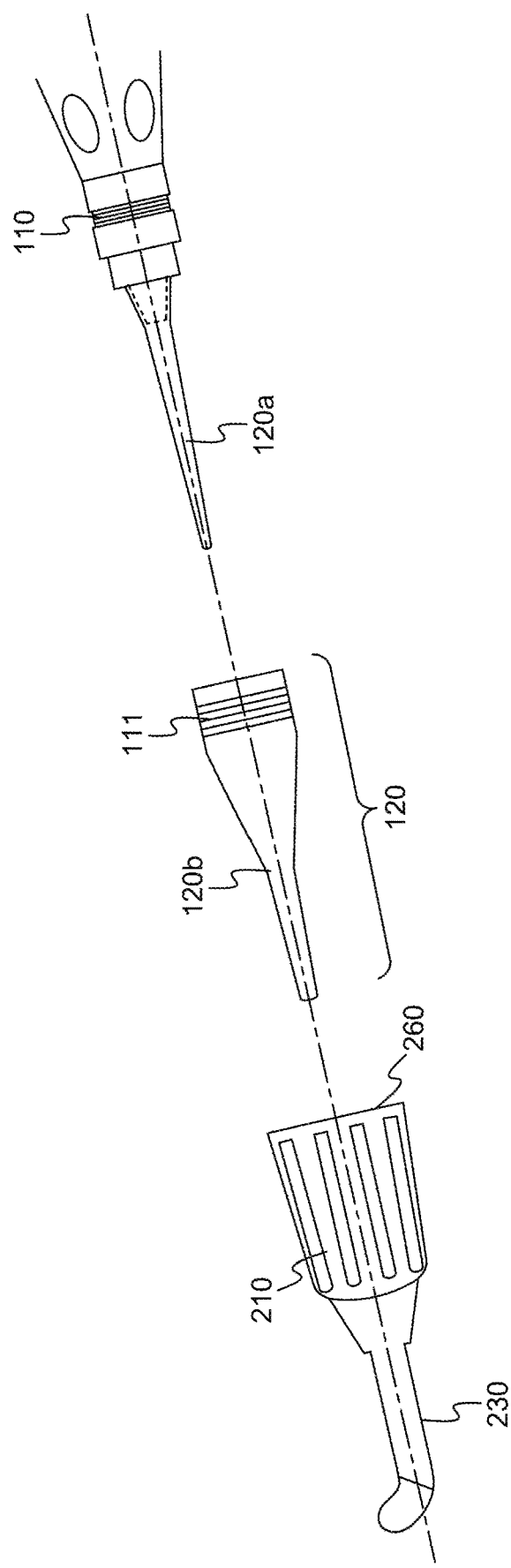
FIG. 5 illustrates an exploded view of an exemplary embodiment of a sleeve and a phacoemulsification needle assembly.

FIG. 5 illustrates an exploded view of FIG. 4b. Phaco sleeve 120b slides over the phaco needle 120a to attach to phaco sleeve attachment means 110. The body portion 210 slides over the phaco sleeve 120b. The attachment means 260 of the body portion 210 attaches to the sleeve attachment means 111.

The tip 230 may be of any shape and may include at least one linear portion to accommodate a linear portion of a phaco needle. The distal end of tip 230 may be rounded and/or may be curved so as to be compatible with use around the edge of the eye and, more particularly, around the edge of the capsular bag. The distal end of tip 230 may also comprise an aspiration port 250 which may be communicatively coupled to the aspiration means provided by the phaco needle assembly 120. Such aspiration means may be provided from the end of the phaco needle assembly 120 at a point below the irrigation port 240, such as at the point demarcated by line 270 (included for illustrative purposes only). Additionally, the diameter of the tip 230 most proximate to the needle end of phaco needle assembly 120 may be of a diameter sufficient to allow the needle end to fit within tip 230 when sleeve 200 is fully engaged with handpiece 100 and to provide sufficient aspiration at and/or through aspiration port 250.

Figure 3:
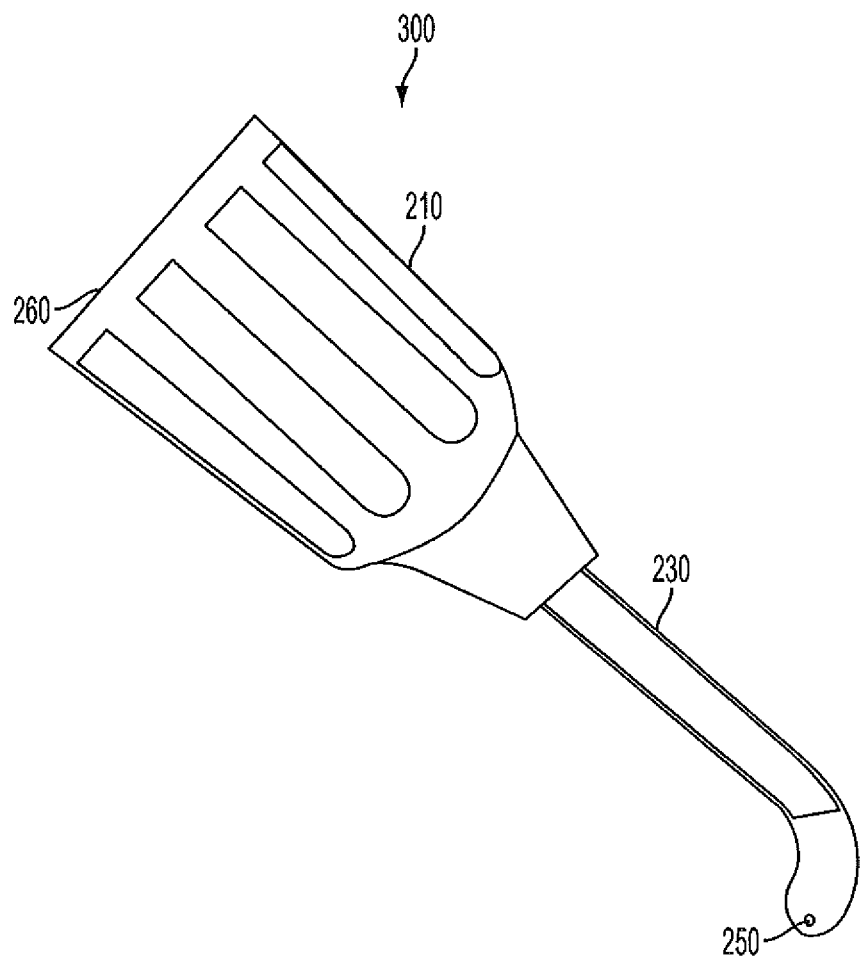
FIG. 3 illustrates an exemplary embodiment of a sleeve for use on a phacoemulsification handpiece.

In some instances, a user may wish to have a handpiece more suitable for bimanual irrigation/aspiration procedures and may wish to have a sleeve which is limited to either irrigation or aspiration. As illustrated in FIG. 3, in an embodiment of the present invention, a sleeve 300 may be implemented as discussed above but may not include an irrigation port and would not require any particular alignment other than successful engagement of the attachment means. As with sleeve 200 discussed above, sleeve 300 may accommodate a variety of needle designs known to those skilled in the art which may be associated with phaco needle assembly 120, which may include, for example, straight, bent, flared, and/or curved tips. The sleeve may have any number of irrigation ports and be of any shape and/or size. It is also envisioned that there may be more than one aspiration port and the aspiration port may be of varying shapes and/or sizes. The diameter of the aspiration port may be less than the diameter of the needle.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure, the protected scope of which is defined by the claims.

What is claimed is:

1. A sleeve for use during an ophthalmic procedure, comprising:
    a body portion having a proximal end and a distal end, the proximal end of the body portion is configured to receive a phacoemulsification sleeve covering a phacoemulsification needle attached to a handpiece, said sleeve adapted to fully enclose the phacoemulsification needle to transform the handpiece from a phacoemulsification handpiece to an irrigation and aspiration handpiece, and the proximal end of the body portion is configured to connect to at least one of the handpiece and the phacoemulsification sleeve at a sleeve attachment; and
    a tip portion having at least one linear portion configured to receive a linear portion of the phacoemulsification sleeve and phacoemulsification needle and a curved distal end portion comprising at least one aspiration port and a rounded end portion at a distal most tip of the curved distal end portion extending beyond the phacoemulsification needle and suitable for use around an edge of a capsular bag of an eye.

2. The sleeve of claim 1, wherein the proximal end of the body portion is removably fixed to the handpiece at the sleeve attachment via a threaded female orifice.

3. The sleeve of claim 1, wherein the body portion comprises at least one grip portion.

4. The sleeve of claim 3, wherein the grip portion is selected from a group consisting of a detent, a raised portion, an etched portion and rubberized plastic.

5. The sleeve of claim 1, wherein the at least one aspiration port is located substantially near the distal most tip of the curved distal end portion of the tip portion.

6. The sleeve of claim 1, wherein the tip portion further comprises at least one irrigation port.

7. The sleeve of claim 6, wherein the irrigation port is located between a proximate end of the tip portion and the aspiration port.

8. The sleeve of claim 6, wherein the at least one irrigation port is located on the at least one linear portion of the tip portion.

9. The sleeve of claim 1, wherein each of the body portion and the tip portion are rigid.

10. The sleeve of claim 1, wherein the body portion further comprises at least one visual alignment aid.

11. The sleeve of claim 1, wherein the tip portion surrounds the phacoemulsification needle and the phacoemulsification sleeve.

12. The sleeve of claim 1, wherein the proximal end of the body portion is removably fixed to the handpiece at the attachment via any one of an adhesive, at least one protrusion and receiving detent, or a locking mechanism.

13. The sleeve of claim 1, wherein the at least one aspiration port has a diameter that is less than a diameter of the phacoemulsification needle.

14. A phacoemulsification system for use during an ophthalmic procedure, comprising:
    a handpiece;
    a phacoemulsification sleeve covering a phacoemulsification needle, the phacoemulsification needle configured to connect to the handpiece; and
    a sleeve that transforms the handpiece from a phacoemulsification handpiece to an irrigation and aspiration handpiece, the sleeve including a body portion and a tip portion,
        the body portion having a proximal end and a distal end, the proximal end of the body portion is configured to receive the phacoemulsification sleeve covering the phacoemulsification needle and is configured to connect to at least one of the handpiece and the phacoemulsification sleeve at a sleeve attachment, and
        the tip portion having at least one linear portion configured to receive a linear portion of the phacoemulsification sleeve and phacoemulsification needle and a curved distal end portion comprising at least one aspiration port and a rounded end portion at a distal most tip of the curved distal end portion extending beyond the phacoemulsification needle and suitable for use around an edge of a capsular bag of an eye.

* * * * *